United States Patent [19]

Lorina et al.

[11] Patent Number: 5,434,122

[45] Date of Patent: Jul. 18, 1995

[54] ROOT AND SYSTEMIC HERBAL TREATMENT FOR IMPROVING THE GROWTH AND/OR YIELD OF PLANTS

[75] Inventors: Marianne Lorina, Costa Mesa, Calif.; Robert H. Rines, Concord, N.H.; Carol M. Rines, Concord, N.H.; Justice C. Rines, Concord, N.H.

[73] Assignee: Allor Foundation, Concord, N.H.

[21] Appl. No.: 105,999

[22] Filed: Aug. 13, 1993

Related U.S. Application Data

[60] Division of Ser. No. 857,447, Mar. 25, 1992, Pat. No. 5,276,005, which is a continuation-in-part of Ser. No. 604,918, Oct. 29, 1990, abandoned.

[51] Int. Cl.$^6$ .................. A01N 35/06; A01N 27/00; A01N 65/00
[52] U.S. Cl. ..................... 504/118; 504/116; 504/142; 504/189; 504/320; 504/348; 504/357; 424/195.1; 71/DIG. 1; 514/690; 514/691; 514/766; 514/783
[58] Field of Search .......... 424/195.1; 504/116, 504/118, 189, 348, 357, 142, 320; 71/DIG. 1; 514/690, 691, 766, 783

[56] References Cited

U.S. PATENT DOCUMENTS

| | | | |
|---|---|---|---|
| 4,136,065 | 1/1979 | Yano et al. | 252/522 |
| 4,442,087 | 4/1984 | Kojima et al. | 424/195.1 |
| 5,176,913 | 1/1993 | Honerlagen et al. | 424/195.1 |
| 5,306,497 | 4/1994 | Dunkel et al. | 424/195.1 |

OTHER PUBLICATIONS

Kaji et al., "A Stimulatory effect of Artemisia Leaf extract on the proliferation of cultured Endothelial cells," Chem. Pharm. Bull., vol. 38(2), Feb. 1990, pp. 538-540.

Okuno et al, "Choleretic Activity of Artemisia Plants," J. Pharm. Soc. Japan, vol. 104(4), Apr. 1984, pp. 384-389.

*Primary Examiner*—Gary E. Hollinden
*Assistant Examiner*—John D. Pak
*Attorney, Agent, or Firm*—Rines and Rines; Robert H. Rines

[57] ABSTRACT

An herbal treatment for plant growth comprising a water solution of extracts of the type withdrawn at elevated temperature from Artemesia plants and the like, applicable to the root structure of plants and as an external spray.

4 Claims, No Drawings

ROOT AND SYSTEMIC HERBAL TREATMENT FOR IMPROVING THE GROWTH AND/OR YIELD OF PLANTS

This application is a division of Ser. No. 07/857,447, filed Mar. 25, 1992 now U. S. Pat No. 5,276,005, which in turn is a continuation-in-part of Ser. No. 07/604,918, filed Oct. 29, 1990, now abandoned.

The present invention relates to methods of and treatments for the root and systemic growth and/or yield improvement of plants, being more specifically concerned with natural herbal plant extractions found useful for such improvements.

BACKGROUND

Earlier work of the Allor Foundation, also assignee of the present invention, on the anti-microbial properties of oil extractions of plant or herbal materials has been referenced in U.S. Pat. No. 4,228,238, such having been found useful when applied topically to living organisms including plants, fruits, animals and humans. Penicillin-like molds developed from extractions of Artemesia genus plants and named *Penicillium Rinesium* and *Penicillium Allorenses*, have been reported by the Foundation in U.S. Pat. No. 3,992,523 (American Type Culture Collection, accession numbers ATCC No. 20398 and 20399).

While it was believed that only the high temperatures of boiling mineral, oil extraction of such Artemesia (212+° C.) and related plant materials could successfully withdraw the several useful herbal essential oil and mixtures (analogously to distillation and condensation processes) to produce the desired effects (for example, charnazuline, thujone, tannins, etc.), it has now been verified that efficacious and useful herbal extractions can be produced at the much lower boiling temperature of water, and in a sufficient quantity and mixture to be beneficial to such living organisms and in particular at least to vegetable and plant growth (tomatoes, peppers, etc.) flowering plants, and elsewhere—and not just as topically applied, but as an actual root treatment in the soil, solution, or other medium in which the plant is grown.

Specifically, significantly faster pre-fruit blossom or pre-plant growth has been attained with the herbal extracts of the invention applied to the plant root system, than with watering alone and than even with some continual conventional chemical plant-food or nutrient additives; and appreciably healthier leaves, blossoms and/or larger fruit and greater yield have been consistently obtained.

OBJECT OF INVENTION

An object of the invention, accordingly, is to provide a new and improved root and systemic herbal treatment for, improving the growth and yield of plants; and, in particular, of vegetable or fruit-bearing plants and flowering plants and the like and with resultant large and healthy blossoms and produce.

A further object is to attain such improved results without the aid of synthetic chemicals but, rather, with natural herbal or plant extractions.

Other and further objects will be explained hereinafter and are more particularly delineated in the appended claims.

SUMMARY

In summary, from one of its important aspects, the invention embraces an herbal treatment for improving the growth of plants, that comprises, treating the plant root by immersion in a water solution of herbal extracts of the type withdrawn at elevated temperature from an Artemesia plant. Preferred and best mode techniques and products are later detailed.

THE INVENTION

As before explained, the withdrawing of the herbal extracts of an appropriate Artemesia plant, as at water distillation temperatures (100° C.), for half an hour or so, produces a mixture of extracts of the type found effective and useful for the purposes of the present invention. A few ounces of preferably dried plant, as of the preferred species *Artemesia arborescens* or *tridentaha*, in several gallons of water (as in ratios later delineated), have been found to generate sufficiently concentrated extracts to be effective in soil-root treatment, as hereinafter explained.

Considering, first, the results attained with vegetable plants—for example, tomatoes and peppers—the roots of the same, as in rich potting soil or earth, are immersed with a water-solution of these elevated temperature extractions, either in seedling or more advanced plant state. It has been found that often only one such immersion is required for the full maturation life of the plant; though in the event of slow growth or less than vigorous leaf or fruit health, one or more further root treatments may be required. Supplementarily, in the latter event, external spray of the extract-containing water solution over the plant and fruit is also useful, including water solution-emulsified oil extractions as before mentioned.

The following tables list one set of several repeated outdoor test results in New England over the past few years, demonstrating the significantly improved growth and yield characteristics imparted by the treatment by the water-extractions of the invention (*Artemesia arborescens*) of tomato plants (labelled Invention), as compared with identical plants planted in the same soil and fertilized conditions, and either, her only watered (Water) or given the same single (or multiple) dose of a water solution of chemical nutrient or plant food (chemical) , marketed under the name "Hyponex".

| Initial Plant Pre-Fruit Growth (Approximate) (Inches) | | | | | |
|---|---|---|---|---|---|
| Height | | | Width | | |
| Water | Chemical | Invention (*Artemisia Arborescens*) | Water | Chemical | Invention |
| Late June | | | | | |
| 8 | 11+ | 12+ | 7 | 9 | 13 |
| Mid July | | | | | |
| 16 | 21 | 27 | 14 | 18 | 28 |

| Fruit Dimensions (approximate average) (Inches) | | | | | |
|---|---|---|---|---|---|
| Major axis (diameter) | | | Depth (thickness) | | |
| Water | Chemical | Invention | Water | Chemical | Invention |
| Late August | | | | | |
| 1.5 | 1.9 | 2.4 | 1.0 | 1.4 | 1.6 |
| Mid-October | | | | | |
| 2.0 | 2.5 | 3.2 | 1.4 | 1.7 | 2.5 |

| Water | Chemical | Invention |
|-------|----------|-----------|
| 32    | 100      | 165       |

While not wanting to be bound by any specific theories as to the mechanisms underlying these improved growth results, it being sufficient to describe the techniques necessary to produce the results of the invention, it may be that the herbal treatment extracts destroy or reduce the efficacy of microorganisms in any or all of the soil and root and system of the plant that otherwise inhibit growth or compete for nutrition, and/or that the extracts provide some measure of systemic nutrition or other needed growth or resistance elements. Again, while not wishing to be bound to particular theories, it being sufficient merely to teach how to get the novel results of the invention, applicants believe they have identified efficacious essential oil thujone, charmazulene and tannin extracts in the particular Artemesia species described herein. Whichever extract component(s) are the effective components, the fact is that the composite extracts of these species do produce applicants' results. Applicants feel comfortable, however, with the importance of their extract identification since the isolative and separation out, for example, of the thujone and charmazuline components in tests of applicants' assignee, the Allot Foundation, proved the individual efficacy of these particular components as anti microbial against various microorganisms.

Improved health and growth has also been attained by the same treatment in the root structure (and, where needed, external spraying) with other vegetables and fruits; namely, pepper (*Artemesia arborescens*) and avocado plants (*Artemesia tridenhata* and *Artemesia arborescens*) in New England; and in California garden tests, with lemons, bananas and oranges (*Artemesia arborescens*) consistently noticeably more fruit than the same trees had ever earlier produced—lemon yield estimated at 25% increase and larger fruits, and oranges and bananas, about 10%. In California, moreover, even in the second and third year after initial root treatment the first year, the improved yield has been observed on tomato plants.

In connection with green pepper plants, above referenced, and a one-half hour 100° C. water extraction of *Artemesia arborescens* (approximately 3 to 5 ounces of dried plant/2–5 gallons of water), the plants reached 9–10" in growth within one month, in June and July, and shortly thereafter 1', as compared with 7" with only watered soil, and also with a greater number of shoots and more inherent green quality. Where green Artemesia plant is used for the extraction, though this is not deemed as preferable as dried plant because of the contained moisture, about 25–50% more plant has been used.

The avocado plant experiment showed far faster and heartier growth with the before-mentioned water extracts in the soil, from 4" in late June to 1½' by late August, and almost 3' by June, and a most uniform leaf distribution not earlier seen.

Rose, jasmin, Bougainvillea and night-blooming cereus plants (particularly the epiphelium species) have also responded well to this treatment of the invention (both with *Artemesia tridentata* and, more strongly with *arborescens*). In particular connection with the latter (and the cereus), growing as a cluster plant in a moist and warm (average 75° F.) greenhouse environment with an adjacent warm pool water, not only have larger and increased yields of blooms been attained, but over much longer periods of the calendar than the usual once or twice a year previously experienced in horticulture—continually from budding in late May and first blooming in early June right into October:

| Blooms    |    |
|-----------|----|
| June      | 7  |
| July      | 8  |
| August    | 4  |
| September | 20 |

In addition to improved growth rate and yield, recovery of poorly growing, bug-eaten rhododendron, with but one *Artemesia arborescens* water extract root treatment, was achieved within a month; a health recovery of ficus plants ("fig") from a yellow, moldy and bug-eaten state to perfectly healthy, clean and green status with additional shoots, within 2 months; rose plants infested with spider bugs, leaf spore and fading, were restored to healthy new growth with no bugs within 2 weeks; jasmin flowering plants with mealy bugs and spot, lost all bugs and spot within less than 2 weeks after a single root treatment with this water extract; and white fly disappeared from Bougainvillea within 3 weeks.

It thus appears that a generic herbal plant treatment is provided by the invention; and further modifications, including other methods of producing the type of extracts withdrawn from the above-identified plants may be used, and that other *Artemesia* or like plants exuding the same extracts as those above described may also be candidates for use in accordance with the teachings herein, such falling within the spirit and scope of the invention as defined in the appended claims.

What is claimed is:

1. An herbal composition for plant growth comprising a water extract solution of herbal extracts withdrawn at an elevated temperature of about 100° C. from a plant selected from the group consisting of *Artemesia arborescens* and *Artemesia tridentata*.

2. An herbal composition for plant growth comprising a water extract solution of herbal extracts withdrawn at an elevated temperature of about 100° C. from *Artemesia arborescens* plant.

3. An herbal composition for plant growth as claimed in claim 1 in which said herbal extracts contain one or more of thujone and chamazulene.

4. An herbal composition for plant growth as claimed in claim 1 in which the concentration of the herbal extracts is that obtained from water extraction with a ratio of *Artemesia* plant-to-water of from about 3 to 5 ounces dry weight-to-2 to 5 gallons.

* * * * *